United States Patent [19]
Harding et al.

[11] Patent Number: 6,166,025
[45] Date of Patent: Dec. 26, 2000

[54] PHARMACEUTICAL COMPOSITIONS CONTAINING ELETRIPTRAN HEMISULPHATE AND CAFFEINE

[75] Inventors: Valerie Denise Harding; Anne Billotte, both of Sandwich, United Kingdom

[73] Assignee: Pfizer Inc., New York, N.Y.

[21] Appl. No.: 09/402,239

[22] PCT Filed: Jul. 1, 1998

[86] PCT No.: PCT/EP98/04176

§ 371 Date: Jan. 27, 2000

§ 102(e) Date: Jan. 27, 2000

[87] PCT Pub. No.: WO99/01135

PCT Pub. Date: Jan. 14, 1999

[30] Foreign Application Priority Data

Jul. 3, 1997 [GB] United Kingdom ............... 9714081
Aug. 28, 1997 [GB] United Kingdom ............... 9718270

[51] Int. Cl.[7] .................................................. A61K 31/40
[52] U.S. Cl. ........................ 514/264; 514/414; 514/415; 514/970
[58] Field of Search ........................... 514/264, 414, 514/415, 970

[56] References Cited

FOREIGN PATENT DOCUMENTS

WO 9606842  3/1996  WIPO ............... C07D 403/06

OTHER PUBLICATIONS

J. Am. Pharm. Association, XLIV (9), 521–527 1955.
Pharm. Acta Helv., 58(1), 28–32 1983.
Pharm. Acta Helv., 58(1), 23–27 1983.
Drug Development and Industrial Pharmacy, 17(11), 1419–36, 1991.

*Primary Examiner*—Frederick Krass
*Attorney, Agent, or Firm*—Peter C. Richardson; Gregg C. Benson; James T. Jones

[57] ABSTRACT

The present invention provides an aqueous pharmaceutical composition comprising 5 to 200 mg/ml of eletriptan hemisulfate and from 0.5 to 2.0% weight/volume of caffeine.

22 Claims, No Drawings

PHARMACEUTICAL COMPOSITIONS CONTAINING ELETRIPTRAN HEMISULPHATE AND CAFFEINE

This is a National Stage filing under 35 USC §371 based on PCT/EP98/04176 which was filed internationally on Jul. 1, 1998.

The present invention relates to pharmaceutical compositions containing eletriptan hemisulphate. More particularly, it relates to aqueous pharmaceutical formulations containing eletriptan hemisulphate that are stabilised by caffeine.

Eletriptan (UK-116,044), 3-([1-methylpyrrolid in-2(R)-yl]methyl)-5-(2-phenylsulphonylethyl)-1H-indole, is a selective $5\text{-}HT_1$-like agonist that is being developed for the treatment of migraine.

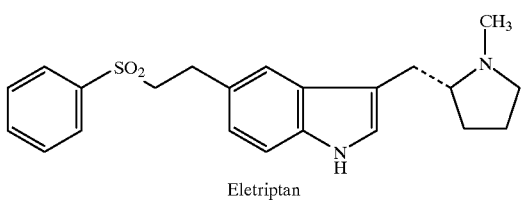

Eletriptan

Eletriptan is described in WO-A-92/06973.

Eletriptan hemisulphate (molecular weight=431.6) has a higher aqueous solubility (>100 mg/ml @ 4° C.) than eletriptan itself and alpha- and beta-polymorphic forms are specifically disclosed in WO-A-96/06842. However, eletriptan hemisulphate is hydrolytically unstable and it is degraded by hydrolysis and oxidation in aqueous solutions. Indeed, a solution of this salt in pH 8 aqueous buffer degrades to leave less than 85% (relative to the original weight) of eletriptan on standing for 12 weeks at 50° C. At least five degradation products have been detected by H.P.L.C. techniques.

This level of stability is highly unsuitable for aqueous pharmaceutical formulations of eletriptan which must have a long shelf-life. Preferably, such formulations should not degrade to leave less than 95% (relative to the original weight) of eletriptan on standing in pH 8 aqueous buffer for 12 weeks at 50° C., and, additionally, the total detectable impurities should not be above 2% by weight after this time.

The object of this invention is to provide a stable, aqueous pharmaceutical formulation containing eletriptan hemisulphate.

A further object of this invention is to provide a stable, aqueous pharmaceutical formulation containing eletriptan hemisulphate that is suitable for intra-nasal and subcutaneous administration and which allows the drug to have good bioavailability and rapid absorption and onset of action when so administered.

Higuchi e al, J. Am. Pharm. Association, XLIV (9), 521 (1955), have reported that caffeine substantially reduces the hydrolytic degradation of benzocaine in aqueous solution.

Samie et al, Pharm. Acta Helv., 58(1), 28 (1983), have shown that caffeine can improve the photochemical stability of certain phenothiazines. However, this is not a general effect for this class of compound. It was similarly found that caffeine also had a variable effect on the non-photochemical degradation of the phenothiazines examined.

It has now been surprisingly found that caffeine stabilises aqueous pharmaceutical formulations containing eletriptan hemisulphate and also improves the solubility thereof.

Further, eletriptan hemisulphate has good bioavailability and rapid absorption and onset of action when administered as caffeine-stabilised formulations by the intra-nasal and subcutaneous routes.

It has also been surprisingly found that the stability of such formulations is further increased by the additional presence of an anti-oxidant (preferably citric acid or ascorbic acid) and/or a co-solvent (preferably ethanol).

The present invention provides an aqueous pharmaceutical composition comprising from 5 to 200 mg/ml of eletriptan hemisulphate and from 0.5 to 2.0% weight/volume of caffeine.

Optionally, an anti-oxidant can be present. Suitable anti-oxidants include citric acid and ascorbic acid. Preferably, up to and including 1.0% weight/volume of citric acid or ascorbic acid can be present.

Optionally, a co-solvent such as ethanol can be present. Preferably, up to and including 20.0% weigh/volume of ethanol can be present.

Preferably, the composition is buffered to a pH of from 4.0 to 9.0.

Preferably, the composition is buffered to a pH of from 7.0 to 9.0.

Preferably, the composition is buffered to a pH of from 7.5 to 8.5.

Preferably, the composition is buffered to about pH 8.

Preferably, the composition is buffered to a pH of from 4.0 to 5.0.

Preferably, from 5 to 150 mg/ml of eletriptan hemisulphate is present.

Preferably, from 10 to 100 mg/ml of eletriptan hemisulphate is present.

Preferably, from 40 to 160 mg/ml of eletriptan hemisulphate is present.

Preferably, from 40 to 140 mg/ml of eletriptan hemisulphate is present.

Preferably, from 60 to 120 mg/ml of eletriptan hemisulphate is present.

Preferably, from 1.0 to 2.0% weight/volume of caffeine is present.

Preferably, from 0.1 to 1.0% weight/volume of citric acid is present.

Preferably, from 0.2 to 1.0% weight/volume of citric acid is present.

Preferably, from 0.3 to 1.0% weight/volume of citric acid is present.

Preferably, from 0.2 to 0.4% weight/volume of citric acid is present.

Preferably, up to and including 1.0% weight/volume of ascorbic acid is present.

Preferably, from 0.3 to 0.6% weight/volume of ascorbic acid is present.

For intra-nasal administration, preferably, from 1.0 to 20.0% weight/volume of ethanol is present, more preferably, from 2.0 to 10.0% weight/volume of ethanol is present and, most preferably, from 2.0 to 6.0% weight/volume of ethanol is present.

For subcutaneous administration, most preferably, up to including 10% weight/volume of ethanol is present.

The compositions of the present invention may be prepared by conventional methods, for example, as described in the Examples hereto. The compositions are buffered to the required pH.

For a composition pH of from 7.0 to 9.0, a suitable buffer such as tris(hydroxymethyl)methylamine can be used. When tris(hydroxymethyl)methylamine is used, its concentration is preferably kept at about 0.05M or about 0.02M and a suitable base, e.g. aqueous sodium hydroxide solution, is used to achieve the required pH level.

For a composition pH of from 4.0 to 6.0, a suitable buffer such as citric acid can be used.

It will be appreciated that any polymorphic or solvate (e.g. hydrate) form of eletriptan hemisulphate can be used for the purpose of the present invention.

Oxidation is one of the main routes of degradation of eletriptan hemisulphate in aqueous solutions. Citric acid and ascorbic acid are well-known anti-oxidants. However, results have shown that the additional presence of an anti-oxidant such as citric acid or ascorbic acid with caffeine further enhances the stability of eletriptan hemisulphate in aqueous solutions, the effect being greater than that attributable purely to the anti-oxidant properties.

Ethanol is primarily present as a co-solvent. However, it has been found that the additional presence of ethanol with caffeine causes an unexpected further increase in the stability of eletriptan hemisulphate in aqueous solutions.

The present compositions are useful for the treatment of a medical condition for which a selective agonist of $5-HT_1$ receptors is indicated, and particularly for the treatment of migraine, hypertension, depression, emesis, anxiety, an eating disorder, obesity, drug abuse, cluster headache, pain, chronic paroxysmal hemicrania, and headache associated with a vascular disorder.

The present compositions are particularly suitable for administration intra-nasally. The nasal route offers a number of advantages such as ease of administration, avoidance of first pass hepatic metabolism, and, particularly, rapid absorption and onset of action.

The normal pH of the nasal secretions in healthy adults ranges from 5.5 to 6.5. For an intra-nasal formulation to have a minimal effect on epithelial integrity, pH, osmolarity and the type and concentration of buffer have to be optimised. A pH of from 4.0 to 9.0 is physiologically acceptable and hypertonic and isotonic solutions seem to produce minimal damage to the nasal mucosa.

The nasal epithelium is a highly vascular tissue, covered by a ciliated pseudostratified columnar epithelium. The nasal mucociliary clearance due to the coordinated movement of cilia is one of the major barriers to an effective intra-nasal delivery. The nasal clearance proceeds at an average rate of about 5–6 mm/min. and, as a result, the residence time within the nasal cavity is only 20–30 minutes. Therefore, nasal deposition as well as the concentration, volume, viscosity and particle size of formulations have to be considered as they could each affect the contact time of formulations in the nasal cavity. Further, the concentrations of caffeine, anti-oxidant (e.g. citric acid) and co-solvent (e.g. ethanol) used are restricted by the level of severity of irritancy or damage that may be caused to the nasal mucosa. Preferably, the required concentration of eletriptan hemisulphate for intra-nasal compositions is about 120 mg/ml. A shelf-life of at least 2 years at room temperature is also desirable.

An illustrative intranasal composition is an aqueous composition comprising:

60 mg/ml of eletriptan hemisulphate,
1.5% weight/volume of caffeine,
0.3% weight/volume of citric acid and
15% weight/volume of ethanol, with the composition buffered to from pH 7.5 to 8.5, preferably about pH 8.0, preferably using tris(hydroxymethyl)methylamine (at a concentration of 0.02M) and sodium hydroxide.

A preferred intranasal composition is an aqueous composition comprising:

120 mg/ml of eletriptan hemisulphate,
1.5% weight/volume of caffeine,
0.3% weight/volume of citric acid and
5% weight/volume of ethanol, with the composition buffered to from pH 7.5 to 8.5, preferably about pH 8.0, preferably using tris(hydroxymethyl)methylamine (at a concentration of 0.05M) and sodium hydroxide.

The proportions of the excipients in the above, preferred, intranasal composition may vary, e.g. the concentration of caffeine can be from 1.0 to 2.0% weight/volume, the concentration of citric acid can be from 0.1 to 1.0% weight/volume and the concentration of ethanol from 0 to 20% weight/volume.

The intra-nasal compositions may be administered using suitable nasal delivery spray devices. Such devices can take the form of metered dose aerosol sprays or mechanical pump sprays not containing any propellant.

The device used directly influences the deposition and residence time of the composition in the nasal cavity. The droplet size generated by the spray device should preferably be from 60 to 80 microns in order to optimise the residence time of the composition in the nasal cavity. Metered spray devices (either monodose or multidose) are preferred since they enable accurate and reproducible delivery of doses.

Airless, mechanical pump devices are preferred since they are designed to protect the formulation from oxidation, dust and/or bacterial contamination. They also obviate the environmental concerns associated with chlorofluorocarbon (CFC) propellants. Such pump devices prevent air entering the drug chamber and create a vacuum after each dispensed dose. The vacuum can produce a deformation of the container which would reduce the volume of the pack with each actuation.

Such devices can also be arranged to keep the drug and the remaining solution in separate chambers until the pump is activated at which point mixing occurs and the composition is administered.

The preferred individual dose of eletriptan hemisulphate when administered by the intra-nasal route is from 1 to 50, more preferably from 1 to 20 and most preferably from 4 to 16 mg per subject. Hence, the above spray devices are usually arranged to deliver from 25 μl to 100 μl of eletriptan hemisulphate in each metered dose or puff.

The present compositions are also suitable for subcutaneous administration which has advantages such as a rapid onset of drug action and avoidance of first pass hepatic metabolism. They are administered by syringe/needle devices under the skin at a suitable site on the body, for example, the thigh region.

The physician will determine the actual dosage that is most suitable for an individual patient and it will vary with the age, weight and response of the particular patient. The above doses are exemplary of the average case. There can, of course, be individual instances where higher or lower dosage ranges are merited.

It will be appreciated that references to treatment include curative, palliative and prophylactic treatment.

The invention is illustrated by the following Examples.

EXAMPLES

The compositions in the following Table 1 were prepared by the addition of tris(hydroxymethyl)methylamine (sufficient quantity to result in a 0.02M concentration in the required composition), caffeine (if required) and citric acid (if required) to water (sufficient quantity to represent 80% of the total volume of the required composition). The mixture was stirred to dissolve the solids and the resulting solution adjusted to the required pH using 1M aqueous sodium hydroxide solution. Eletriptan hemisulphate was added and stirring continued until dissolution was achieved. The pH was then re-adjusted to the required pH, if necessary, using 1M aqueous sodium hydroxide solution. Ethanol (if required) was then added and the solution made up to the required final volume with water.

TABLE 1

| Example no. | pH | Eletriptan hemisulphate (mg/ml) | Caffeine (% w/v) | Citric acid (% w/v) | Ethanol (% w/v) |
|---|---|---|---|---|---|
| 1 | 8.0 | 60 | 1.5 | 0.3 | 15 |
| 2 | 8.0 | 10 | 1.5 | 0.3 | 15 |
| 3 | 8.0 | 10 | 1.0 | — | — |
| 4 | 8.0 | 10 | 1.0 | 0.3 | — |
| 5 | 8.0 | 10 | 1.0 | 0.3 | 10 |
| Reference A[1] | 8.0 | 10 | — | — | — |
| Reference B[2] | 8.0 | 10 | — | 0.3 | — |
| Reference C | 8.0 | 10 | — | — | 10 |
| Reference D | 8.0 | 10 | — | 0.3 | 10 |

Footnotes
[1,2]Precipitation of solutes occurred from these compositions on storage (see Table 2).

Example 6

An aqueous composition of pH8 containing 120 mg/ml of eletriptan hemisulphate, 1.5% w/v of caffeine, 0.3% w/v of citric acid and 5% w/v of ethanol was prepared as follows.

Tris(hydroxymethyl)methylamine (sufficient quantity to result in a 0.05M concentration in the required composition), citric acid, ethanol and caffeine were added to water (sufficient quantity to represent 80% of the total volume of the required composition). The mixture was stirred to dissolve the solids and the resulting solution adjusted to pH8 using 5M aqueous sodium hydroxide solution. Eletriptan hemisulphate was added and stirring continued until dissolution was achieved. The pH was then re-adjusted to the required pH, if necessary, using 5M aqueous sodium hydroxide solution. The solution was then made up to the required final volume with water.

PREPARATION 1

Eletriptan Hemisulphate

A stirred solution of eletriptan (90.0 g, 0.235 mol) in acetone (3195 ml) was cooled to 0–4° C. and concentrated sulphuric acid (11.77 g, 0.118 mol) added,. dropwise over a 30 minute period under a nitrogen atmosphere, maintaining the temperature at 0–4° C. throughout the addition. The resulting slurry was granulated at 0–4° C. for 2 hours, filtered and the solid washed with acetone (2×90 ml). The product was dried under reduced pressure at 40° C. overnight (93.7 g).

Eletriptan hemisulphate obtained by the above procedure can be crystallised as follows.

Eletriptan hemisulphate (104.3 g) was dissolved in demineralised water (188 ml) with stirring and acetone (1043 ml) added. The solution was heated to the reflux temperature and the reflux maintained during the addition of acetone (1564 ml) over a 40 minute period. The solution was cooled to room temperature and seeded. Stirring was continued for 30 minutes and then further acetone (2085 ml) added to the slurry over 30 minutes. The mixture was cooled to 0–4° C. and granulated for 1.5 hours. The solid was filtered off, washed with acetone (2×130 ml) and dried under reduced pressure at 40° C. (93.21 g).

STABILITY STUDIES

Samples of the compositions set out in Table 1 were stored for 12 weeks at 50° C.

After this time, each sample was analysed by HPLC using the conditions set out below and the results are presented in Table 2.

Chromatoaraphic Conditions:
Column:15 cm×0.46 cm i.d. stainless steel containing Hypersil BDS C8 (trade mark), 5 micrometer packing, or equivalent.
Mobile phase:0.02 M aqueous ammonium acetate solution: methanol (65:35, by volume). The pH of the mixture was adjusted to 6.0 with glacial acetic acid.
Operating Temperature:30° C.
Flow Rate:1.0 ml/min.
Detection:Ultraviolet spectrophotometric detector operating at 225 nm.
Sample Size:10 microliters. A suitable injector wash solution is methanol/water (50:50, by volume).
Retention Time:Under the conditions described, eletriptan elutes approximately 12.5–14.5 minutes after injection.
Run Time:30 minutes for a typical stability assessment.

TABLE 2

| Example no. | Eletriptan remaining (wt. %) | Total detectable impurity[4] (wt. %) |
|---|---|---|
| 1 | 96.7 | 1.7 |
| 2 | 97.0 | 2.0 |
| 3 | 90.7 | 2.5 |
| 4 | 91.8 | 3.0 |
| 5 | 95.1 | 2.4 |
| Reference A[1,3] | — | — |
| Reference B[2] | — | — |
| Reference C | 90.2 | 2.4 |
| Reference D | 52.9 | 1.4 |

Footnotes
[1,2]Meaningful stability measurements could not be carried out on these compositions since precipitation of solutes occurred before expiry of the storage period.
[3]In a parallel study, a stable solution was achieved on preparing a composition corresponding exactly to Reference A in Table 1 by the same specified method. After storage for 12 weeks at 50° C., use of the above analytical method showed that 80.49 wt. % of eletriptan remained and the total detectable impurity was 3.0 wt. %.
[4]Not all the impurities that formed were detectable by the analysis method used.

Discussion of the Results in Table 2

These results clearly show that caffeine stabilises aqueous formulations containing eletriptan hemisulphate and also improves the solubility thereof.

These results also show that citric acid and ethanol, both when present separately or together, provide enhanced stability of such formulations.

The result for Reference C shows that ethanol appears to have a stabilising effect on aqueous formulations of eletriptan hemisulphate.

What is claimed is:

1. An aqueous pharmaceutical composition comprising from 5 to 200 mg/ml of eletriptan hemisulphate and from 0.5 to 2.0% weight/volume of caffeine.

2. A composition as claimed in claim 1 comprising from 40 to 160 mg/ml of eletriptan hemisulphate.

3. A composition as claimed in claim 1 comprising from 60 to 120 mg/ml of eletriptan hemisulphate.

4. A composition as claimed in claim 1 comprising from 1.0 to 2.0% weight/volume of caffeine.

5. A composition as claimed in claim 1 further comprising an anti-oxidant.

6. A composition as claimed in claim 5 wherein the anti-oxidant is citric acid.

7. A composition as claimed in claim 6 wherein up to and including 1.0% weight/volume of citric acid is present.

8. A composition as claimed in claim 7 wherein from 0.2 to 0.4% weight/volume of citric acid is present.

9. A composition as claimed in claim 5 wherein the anti-oxidant is ascorbic acid.

10. A composition as claimed in claim 1 further comprising ethanol.

11. A composition as claimed in claim 10 wherein up to and including 20.0% weight/volume of ethanol is present.

12. A composition as claimed in claim 11 wherein from 2.0 to 10.0% weight/volume of ethanol is present.

13. A composition as claimed in claim 12 wherein from 2.0 to 6.0% weight/volume of ethanol is present.

14. A composition as claimed in claim 1 that is buffered to a pH of from 4.0 to 9.0.

15. A composition as claimed in claim 14 that is buffered to a pH of from 7.5 to 8.5.

16. A composition as claimed in claim 14 that is buffered to a pH of from 4.0 to 5.0.

17. A composition as claimed in claim 1 comprising
   120 mg/ml of eletriptan hemisulphate,
   1.5% weight/volume of caffeine,
   0.3% weight/volume of citric acid and
   5% weight/volume of ethanol,
   with the composition buffered to from pH 7.5 to 8.5.

18. A composition as claimed in claim 17 wherein it is buffered using tris(hydroxymethyl)methylamine and sodium hydroxide.

19. A method of treatment of a human for a disease or condition for which adminisration of a selective agonist of 5-$HT_1$ receptors is indicated which comprises administering to said human an effective amount of a composition as claimed in claim 1.

20. A method of treatment of a human for a disease or condition selected from the group consisting of migraine, hypertension, depression, emesis, anxiety, an eating disorder, obesity, drug abuse, cluster headache, pain, chronic paroxysmal hemicrania and headache associated with a vascular disorder, which comprises administering to said human an effective amount of a composition as claimed in claim 1.

21. A method as claimed in claim 20 for treating migraine.

22. A composition as claimed in claim 17, buffered to a pH of about 8.0.

* * * * *